US012580080B2

(12) United States Patent
Shen et al.

(10) Patent No.: US 12,580,080 B2
(45) Date of Patent: Mar. 17, 2026

(54) PLASMA piRNA COMBINATION FOR EARLY DIAGNOSIS OF GASTRIC CANCER AND APPLICATION THEREOF

(71) Applicant: THE FIRST AFFILIATED HOSPITAL OF WENZHOU MEDICAL UNIVERSITY, Wenzhou (CN)

(72) Inventors: Xian Shen, Wenzhou (CN); Jianjian Zheng, Wenzhou (CN); Xiaodong Chen, Wenzhou (CN); Lifan Lin, Wenzhou (CN); Feng Jiang, Wenzhou (CN); Xinmiao Li, Wenzhou (CN); Qiqi Tao, Wenzhou (CN); Weizhi Zhang, Wenzhou (CN)

(73) Assignee: THE FIRST AFFILIATED HOSPITAL OF WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 18/901,053

(22) Filed: Sep. 30, 2024

(65) Prior Publication Data

US 2025/0322953 A1     Oct. 16, 2025

Related U.S. Application Data

(63) Continuation of application No. PCT/CN2024/095385, filed on May 27, 2024.

(30) Foreign Application Priority Data

Apr. 16, 2024     (CN) .......................... 202410453138.0

(51) Int. Cl.
*G16H 50/20* (2018.01)
*C12N 15/113* (2010.01)

(52) U.S. Cl.
CPC ........... *G16H 50/20* (2018.01); *C12N 15/113* (2013.01); *C12N 2310/14* (2013.01)

(58) Field of Classification Search
CPC .............................. G16H 50/20; C12N 15/113
See application file for complete search history.

(56) References Cited

FOREIGN PATENT DOCUMENTS

| | | |
|---|---|---|
| CN | 101289692 A | 10/2008 |
| CN | 101289693 A | 10/2008 |
| CN | 109072240 A | 12/2018 |
| WO | 2016065349 A2 | 4/2016 |

OTHER PUBLICATIONS

Tatiana Vinasco-Sandoval, et al., Global Analyses of Expressed Piwi-Interacting RNAs in Gastric Cancer, International Journal of Molecular Sciences, 2020, pp. 1-16, vol. 21.
Xiandong Lin, et al., Transcriptome-wide piRNA profiling in human gastric cancer, Oncology reports, 2019, pp. 3089-3099, vol. 41.
Angélique Girard, et al., A germline-specific class of small RNAs binds mammalian Piwi proteins, Nature, 2006, pp. 199-202, vol. 442.

*Primary Examiner* — Jerry Lin
(74) *Attorney, Agent, or Firm* — Bayramoglu Law Offices LLC

(57)     ABSTRACT

A plasma piwi-interacting RNA (piRNA) combination for early diagnosis of gastric cancer and application thereof are provided. Based on the plasma piRNA expression profile of the Chinese population, the present invention obtains a plasma piRNA combination for early diagnosis of gastric cancer, and establishes an early diagnosis model for gastric cancer based on the plasma piRNA combination. The model can predict the incidence risk of gastric cancer with relatively high accuracy, which helps to reduce the cost of detection. At the same time, the present invention uses a Lasso Logistic regression model, which greatly reduces the number of variables included in the model and facilitates the application and popularization of the model.

3 Claims, 4 Drawing Sheets

Specification includes a Sequence Listing.

1

PLASMA piRNA COMBINATION FOR EARLY DIAGNOSIS OF GASTRIC CANCER AND APPLICATION THEREOF

CROSS REFERENCE TO THE RELATED APPLICATIONS

This application is a continuation application of International Application No. PCT/CN2024/095385, filed on May 27, 2024, which is based upon and claims priority to Chinese Patent Application No. 202410453138.0, filed on Apr. 16, 2024, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBHZWH008-PKG_SequenceListing.xml, created on Sep. 26, 2024, and is 11,491 bytes in size.

TECHNICAL FIELD

The present invention relates to the technical field of bioinformatics, and in particular to a plasma piwi-interacting RNA (piRNA) combination for early diagnosis of gastric cancer and application thereof.

BACKGROUND

Gastric cancer is one of the most common malignant tumors in China. In recent years, the incidence of gastric cancer in China has been gradually increasing, seriously threatening the lives and health of residents. Screening, early diagnosis, and early treatment for people at high risk of gastric cancer can effectively reduce the incidence and mortality of gastric cancer.

The traditional screening and diagnosis model of gastric cancer is: initial screening with hematology, and those who are positive in the initial screening are diagnosed by endoscopic biopsy, which is the gold standard method. Although traditional pathological examination has a certain degree of accuracy, it is an invasive method, which brings many inconveniences to patients and even causes complications and sequelae such as bleeding and infection. Compared with pathological examination, the development of blood markers has brought convenience to the screening and diagnosis of gastric cancer, and the results are more stable and have the characteristics of high patient compliance. The wide application of detecting pepsinogen, gastrin-17, *Helicobacter pylori* (HP), and tumor markers at present shows the potential of biomarkers in the screening and diagnosis of gastric cancer. Therefore, it is urgent to explore more effective, accurate, sensitive, and non-invasive clinical biomarkers for the early screening and diagnosis of gastric cancer.

Piwi-interacting RNA (piRNA) is a non-coding RNA with a length of 25 to 33 nt, which is closely related to the maintenance of genome stability, epigenetic regulation, germ stem cell differentiation, embryonic development, and the occurrence and development of various diseases. Therefore, piRNA has the potential as a biomarker. At present, the relevant content of piRNA in gastric cancer patients still needs further study. A better understanding of the role of piRNA in the occurrence and development of gastric cancer can explore new biomarkers for early screening and diagnosis of gastric cancer, which is important for the early screening and diagnosis of gastric cancer patients.

SUMMARY

The purpose of the present invention is to provide a plasma piRNA combination for early diagnosis of gastric cancer and application thereof. The present invention provides a plasma piRNA combination for early diagnosis of gastric cancer, and establishes and verifies a model for early diagnosis of gastric cancer based on the results, which is convenient for early screening.

Technical solution of the present invention: A plasma piRNA combination for early diagnosis of gastric cancer, where the plasma piRNA in the plasma piRNA combination includes: hsa-piR-32885, hsa-piR-3440, hsa-piR-786, hsa-piR-12390, hsa-piR-414, hsa-piR-23197, hsa-piR-32911, hsa-piR-32945, hsa-piR-28060, hsa-piR-7096, hsa-piR-32870, and hsa-piR-30778.

Application of the above plasma piRNA combination for early diagnosis of gastric cancer in constructing a model for early diagnosis of gastric cancer.

In the aforementioned application, the gastric cancer early diagnosis model is a Lasso Logistic regression model.

In the aforementioned application, the mathematical expression of the Lasso Logistic regression model is as follows:

$$\text{Gastric cancer incidence risk score} =$$

$$\sum(\text{plasma } piRNA \text{ expression value} \times \text{regression coefficient}).$$

In the aforementioned application, the regression coefficients are as follows:

The regression coefficient of hsa-piR-32885 is −0.001;
The regression coefficient of hsa-piR-3440 is −0.039;
The regression coefficient of hsa-piR-786 is −0.007;
The regression coefficient of hsa-piR-12390 is −0.001;
The regression coefficient of hsa-piR-414 is −0.002;
The regression coefficient of hsa-piR-23197 is 0.037;
The regression coefficient of hsa-piR-32911 is 0.008;
The regression coefficient of hsa-piR-32945 is 0.004;
The regression coefficient of hsa-piR-28060 is 0.001;
The regression coefficient of hsa-piR-7096 is 0.002;
The regression coefficient of hsa-piR-32870 is 0.002;
The regression coefficient of hsa-piR-30778 is 0.026.

In the aforementioned application, the Lasso Logistic regression model construction method is as follows:

(1) collecting plasma from gastric cancer patients and healthy control groups, respectively extracting plasma free piRNA; (2) using piRNA transcriptome sequencing to obtain plasma piRNA expression profiles; (3) randomly dividing gastric cancer patients and healthy control groups into a training set and a test set, establishing a Lasso Logistic regression model in the training set, and obtaining the piRNA regression coefficients included in the model; (4) based on the Lasso Logistic regression model established in the training set, using the receiver operating characteristic (ROC) curve, sensitivity and specificity indicators in the test set to evaluate the prediction accuracy of the model.

Compared with the prior art, the innovation of the present invention is that based on the plasma piRNA expression profile of the Chinese population, a plasma piRNA combination for early diagnosis of gastric cancer is obtained, and an early diagnosis model for gastric cancer is established based on the plasma piRNA combination. The model predicts that the area under the curve (AUC) of gastric cancer is 0.96, the sensitivity is 90%, and the specificity is 96%, which can effectively distinguish gastric cancer patients from healthy controls. In addition, the Lasso Logistic regression model is used in the present invention to greatly reduce the number of variables included in the model, which will help reduce the cost of detection and promote the application of the model. The present invention is carried out by blood testing, which is convenient and fast, with small trauma area, convenient use and good stability. Only 200 μL of plasma is required each time, avoiding the risk of physical damage to the patient caused by multiple tissue biopsies through gastroscopy to obtain tumor tissue for pathological identification, greatly reducing the cost of detection.

DETAILED DESCRIPTIONS OF THE EMBODIMENTS

The present invention is further described below in conjunction with the accompanying drawings and embodiments, but is not intended to be limiting of the present invention.

Embodiment: Construction and verification of an early diagnosis model for gastric cancer based on plasma piRNA expression profile.

Figure 1:
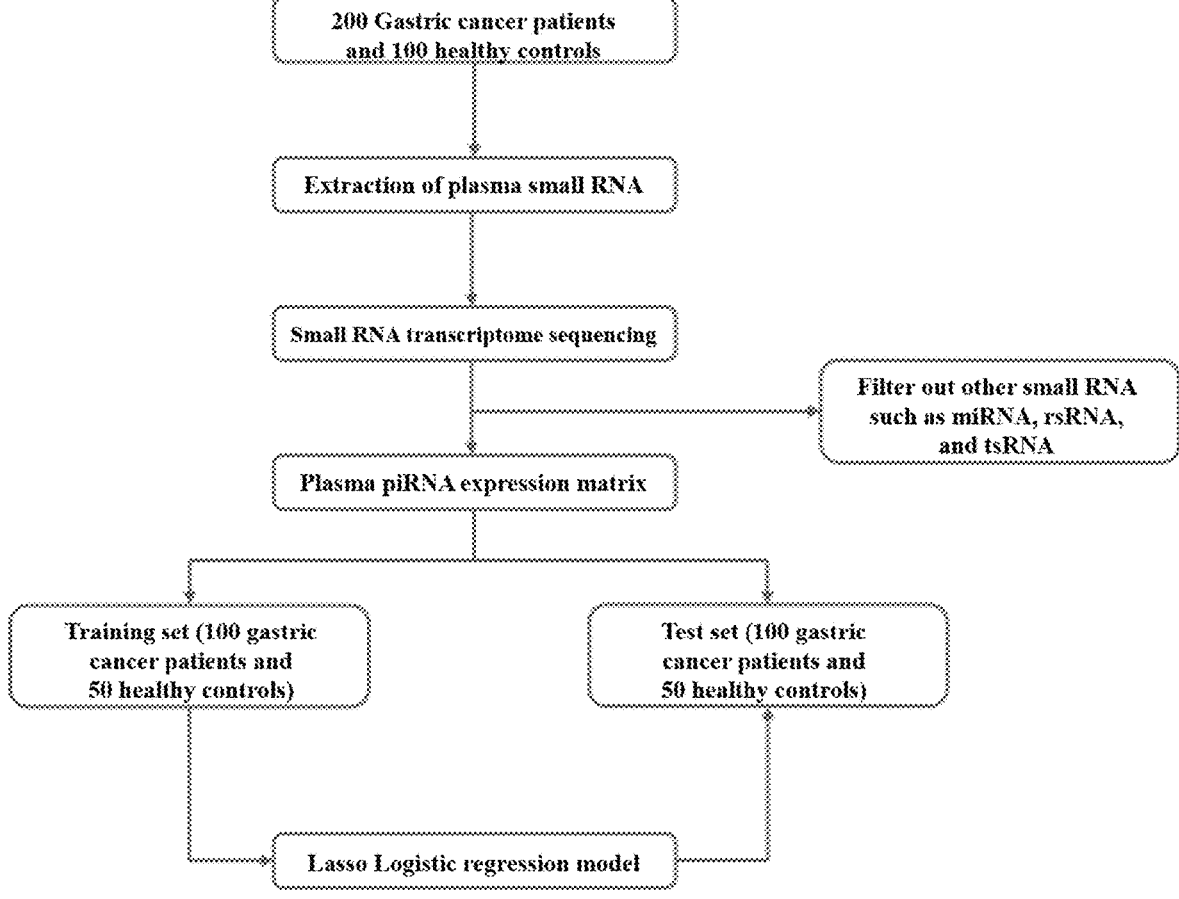
FIG. 1 is a schematic diagram of the technical solution of the present invention.

This embodiment is divided into four parts: collecting plasma samples, extracting plasma small RNA using the Qiagen miRNeasy plasma kit, sequencing small RNA transcriptomes, and establishing a Lasso Logistic regression model based on the plasma piRNA expression matrix. The process of this embodiment is shown in FIG. 1.

(1) Collecting Plasma Samples;

5 mL of whole blood was collected from 200 gastric cancer patients and 100 healthy controls and was placed in a blood collection tube containing EDTA anticoagulant. After the collection is completed, repeatedly invert the blood collection tube to fully mix the EDTA anticoagulant with the blood. Centrifuge at 3000 rpm and 4° C. for 10 min, and the supernatant is plasma. 2 mL of plasma was taken, placed in an EP tube, and store it in a −80° C. refrigerator.

(2) Extraction of Plasma Small RNA Using Qiagen miRNeasy Plasma Kit;

Cell lysis and small RNA extraction: Adding 1 mL of QIAzol lysis reagent to 200 μL of sample, vortexing or inverting to mix the liquid, and incubating at room temperature (15-25° C.) for 5 min; adding 200 μL of chloroform, shaking vigorously for 15 s, and incubating at room temperature for 2-3 min; after incubation, centrifuging at 12000 g for 15 min at 4° C.; after centrifugation, transferring the upper aqueous phase to a new EP tube, adding 100% ethanol with a volume that is 1.5 times the volume of the aqueous phase, and mixing the two thoroughly by inverting; pipetting 700 μL of liquid into RNeasy MinElute spin column, centrifuging at 8000 g for 15 s at room temperature, and discarding the waste liquid in the collection tube; repeating the above steps with the remaining liquid; adding 700 μL of Buffer RWT to RNeasy MinElute spin column, centrifuging at 8000 g for 15 s, and discarding the waste liquid in the collection tube; pipetting 500 μL buffer RPE into the RNeasy MinElute spin column, centrifuging at 8000 g for 15 s, and discarding the waste liquid in the collection tube; adding 500 μL of ethanol with a mass fraction of 80% to the RNeasy MinElute spin column, centrifuging at 8000 g for 2 min, and discarding the waste liquid in the collection tube; placing the RNeasy MinElute spin column in a new 2 mL EP tube, opening the spin column cover, adjusting the centrifuge speed to the maximum, centrifuging for 5 min, and discarding the waste liquid in the collection tube and collection tube; place the RNeasy MinElute spin column in a new 1.5 mL collection tube.

Small RNA elution: Adding 15 μL RNase-free water in the middle of the filter membrane, gently covering the tube cap, letting stand at room temperature for 2 min, centrifuging at maximum speed for 1 min. The bottom of the tube is the separated RNA.

RNA concentration and RNA integrity assessment: 1 μL was taken for Aglient 2100 RNA Pico chip detection, and the peak value was generally below 200 nt. Only high-quality RNA samples (RIN≥7, >50 ng/μL, OD260/280 between 1.8 and 2.2) were used to construct sequencing libraries.

(3) Small RNA Transcriptome Sequencing;

Small RNA quantification: The small RNA samples used for library construction were first quantified using a library quantification kit. 1 μg was used as the starting material to generate the sequencing library.

Connection of adapter sequences: The adapter sequences were linked at the 3' and 5' ends respectively.

cDNA synthesis: Under the action of MMLV-derived PrimeScript reverse transcriptase (RT), random primers were used to reversely synthesize the first-strand cDNA using the RNA after the connection of the adapters as a template, followed by second-strand synthesis to form a stable double-stranded structure.

Library enrichment: PCR amplification (11-12 cycles) was performed using sequencing primers to enrich the library concentration.

Library purification: According to the length distribution characteristics of small RNA, the target fragments were recovered by gel cutting (6% Novex TBE PAGE gel, 1.0 mm, 10 wells).

Sequencing and data analysis: Qubit 4.0 quantification, mixing according to data ratio; bridge PCR amplification on cBot to generate clusters; sequencing on Illumina NovaSeq 6000 platform.

(4) Bioinformatics Analysis;

Raw sequence data statistics: Illumina sequencing belongs to the second-generation sequencing technology. A single run can generate billions of reads. Such a large amount of data cannot show the quality of each read one by one. Using statistical methods, the base distribution and quality fluctuation statistics of each cycle of all sequencing reads can intuitively reflect the sequencing quality and library construction quality of the sample from a macro perspective. Sequencing-related quality assessment was performed on the raw sequencing data of each sample, including: A/T/G/C base content distribution statistics, base quality distribution statistics, and base error rate distribution statistics.

Quality control of raw sequencing data: The raw sequencing data contains sequencing adapter sequences or low-quality reads. To ensure the accuracy of subsequent bioinformatics analysis, the raw sequencing data was first filtered to obtain high-quality sequencing data to ensure the smooth progress of subsequent analysis. The specific steps and order are as follows: 1) removing 3' adapter sequence in the reads, and removing reads without inserted fragments due to reasons such as adapter self-ligation; 2) cutting the bases with low sequencing quality at the 3' end (quality value less than 20); 3) removing reads containing unknown base N; 4) removing reads that were too short (<18 nt); and 5) removing reads that were too long (>32 nt); after quality control, analyzing the length of clean reads, and selecting reads with a length of 18-32 nt as useful reads for subsequent analysis based on the characteristics of small RNA.

Align with the reference genome: Using Bowtie to align the useful reads after quality control with the specified reference genome (human genome), and then aligning the reads to the piRBase database to calculate the plasma piRNA expression matrix.

Compared with the traditional Logistic regression model, the biggest difference between the Lasso Logistic regression model and the traditional Logistic regression model is that the Lasso Logistic regression model introduces the regularization parameter 2 of the regression coefficient. By adjusting the parameter λ value, the regression coefficient of some variables can be equal to 0 (making the regression coefficient of other piRNA except the piRNA shown in Table 1 equal to 0), achieving the purpose of variable screening and facilitating the application and popularization of the model.

Figure 2:
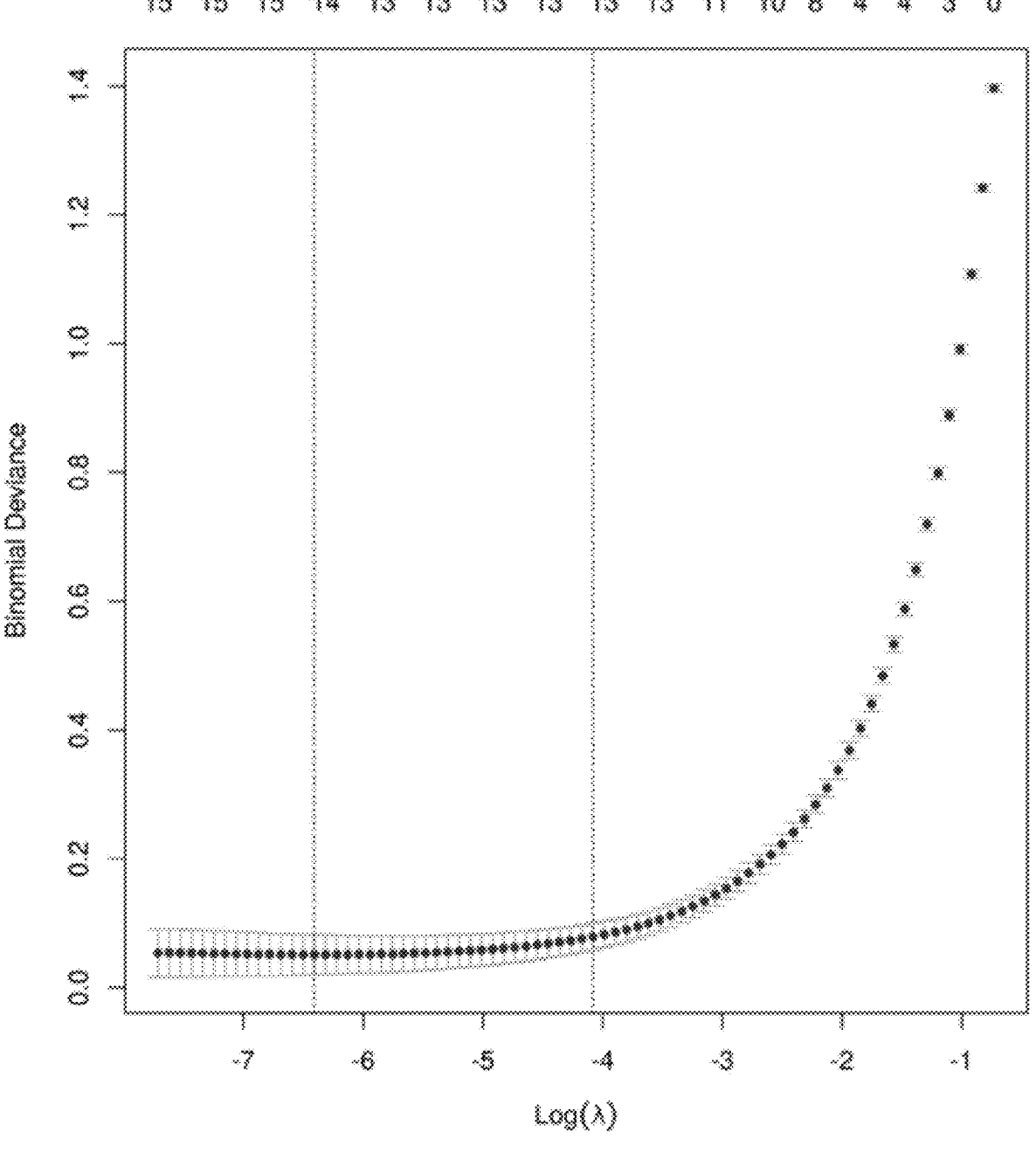
FIG. 2 is a diagram showing the relationship between the regularization parameter λ and the partial likelihood estimation deviation in the Lasso Logistic regression model.

The optimal λ value was determined by using a 20-fold cross-validation method in the training set. When this 2 value was taken, the partial likelihood estimation deviation of the Lasso Logistic regression model was minimal, as shown in FIG. 2. It was found that when this A value was taken, the regression coefficients of 783 piRNA were equal to 0, and the regression coefficients of 12 piRNA were not 0. The sequences of these 12 piRNA and their regression coefficients are shown in the table.

TABLE 1

Regression coefficients of piRNA in Lasso Logistic regression model

| piRNA | piRNA base sequence | Regression coefficients of piRNA |
|---|---|---|
| hsa-piR-32885 | CACCAGTGTGAGTTCTACCATTGCCAAA (SEQ ID NO: 1) | −0.001 |
| hsa-piR-3440 | TCAGACATTTGGTGTATGTGCTTGGC (SEQ ID NO: 2) | −0.039 |
| hsa-piR-786 | ACTTGTGATGTCTTCAAAGGAACCACTGATG (SEQ ID NO: 3) | −0.007 |
| hsa-piR-12390 | CAGCAGTTGAACATGGGTCAGTCGGTCC (SEQ ID NO: 4) | −0.001 |
| hsa-piR-414 | ACAGCAGTTGAACATGGGTCAGTCGGTCC (SEQ ID NO: 5) | −0.002 |
| hsa-piR-23197 | CCTCCCAAAGTGCTGGGATTACAGGCGTGAG (SEQ ID NO: 6) | 0.037 |
| hsa-piR-32911 | CCTGGACTCAAGCGATCCTCCAGCCTCAGCCT (SEQ ID NO: 7) | 0.008 |
| hsa-piR-32945 | GCGTGCCTGTAGTCCCAGCTACTCGGG (SEQ ID NO: 8) | 0.004 |
| hsa-piR-28060 | GGCCGTGATCGTATAGTGGTTAGTAC (SEQ ID NO: 9) | 0.001 |
| hsa-piR-7096 | TCGGCATCAATATGGTGACCTCCCGGG (SEQ ID NO: 10) | 0.002 |
| hsa-piR-32870 | AGGGTGGTTCAGTGGTAGAATTCTCG (SEQ ID NO: 11) | 0.002 |
| hsa-piR-30778 | TACTTTGGGAGGCTGAGGCGGGTGGAT (SEQ ID NO: 12) | 0.026 |

A Lasso Logistic regression model was established based on the plasma piRNA expression matrix;

After obtaining the plasma piRNA expression matrix, all samples were randomly divided into a training set and a test set at a ratio of 50% and 50%, and a Lasso Logistic regression model was constructed in the training set. Then, the prediction accuracy of the model was evaluated using indicators such as AUC, sensitivity, and specificity in the training set and the test set. The software used was the glmnet package of the R language program.

The regression coefficient value of each piRNA expression value indicates the change in the subject's gastric cancer incidence risk score for every 1 unit change in the expression of the piRNA. If the regression coefficient is a positive number, it means that the incidence risk of gastric cancer increases when the piRNA expression value increases; similarly, if the regression coefficient is a negative number, it means that the incidence risk of gastric cancer decreases when the piRNA expression value increases. The mathematical calculation formula for the gastric cancer incidence risk score is:

Gastric cancer incidence risk score (Lasso_Logistic_Score) =

$$\sum (\text{plasma } piRNA \text{ expression value} \times \text{regression coefficient}).$$

Figure 3:
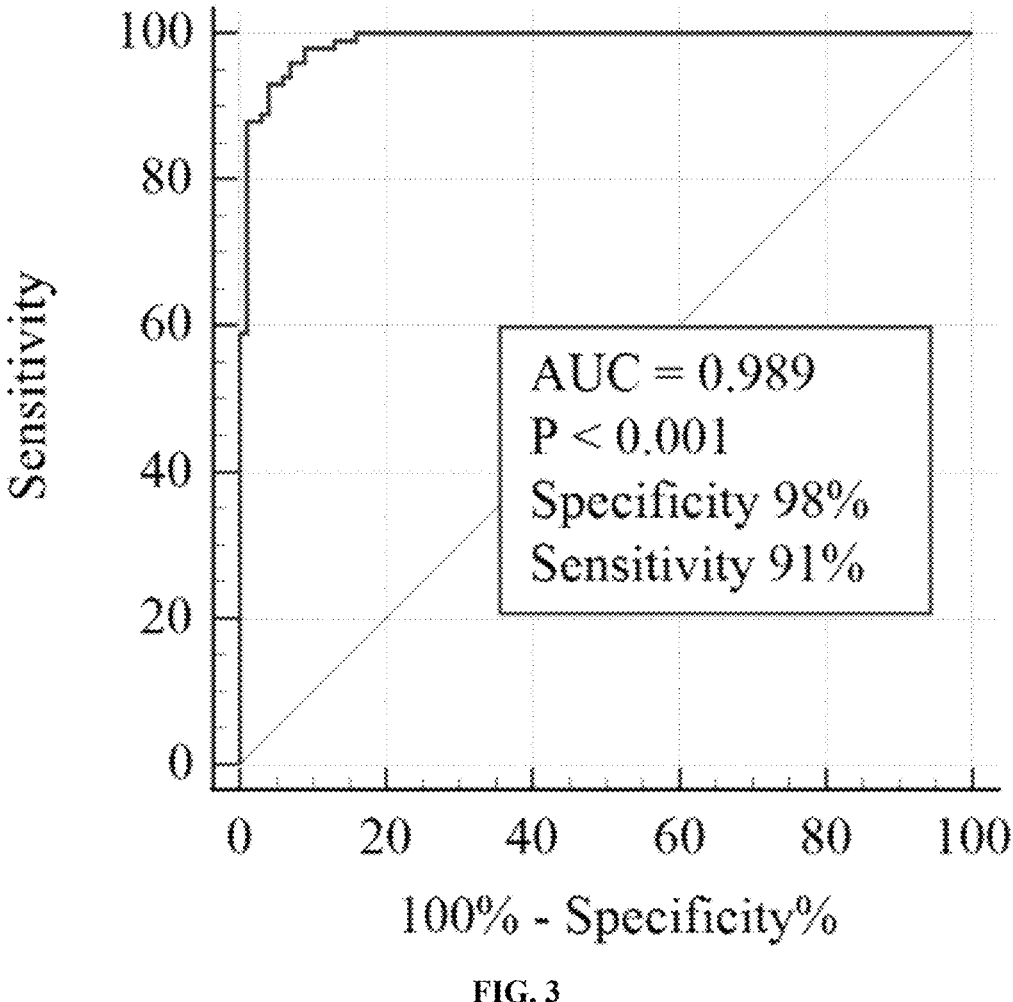
FIG. 3 is a schematic diagram of the ROC curve of the model in the training set.
Figure 4:
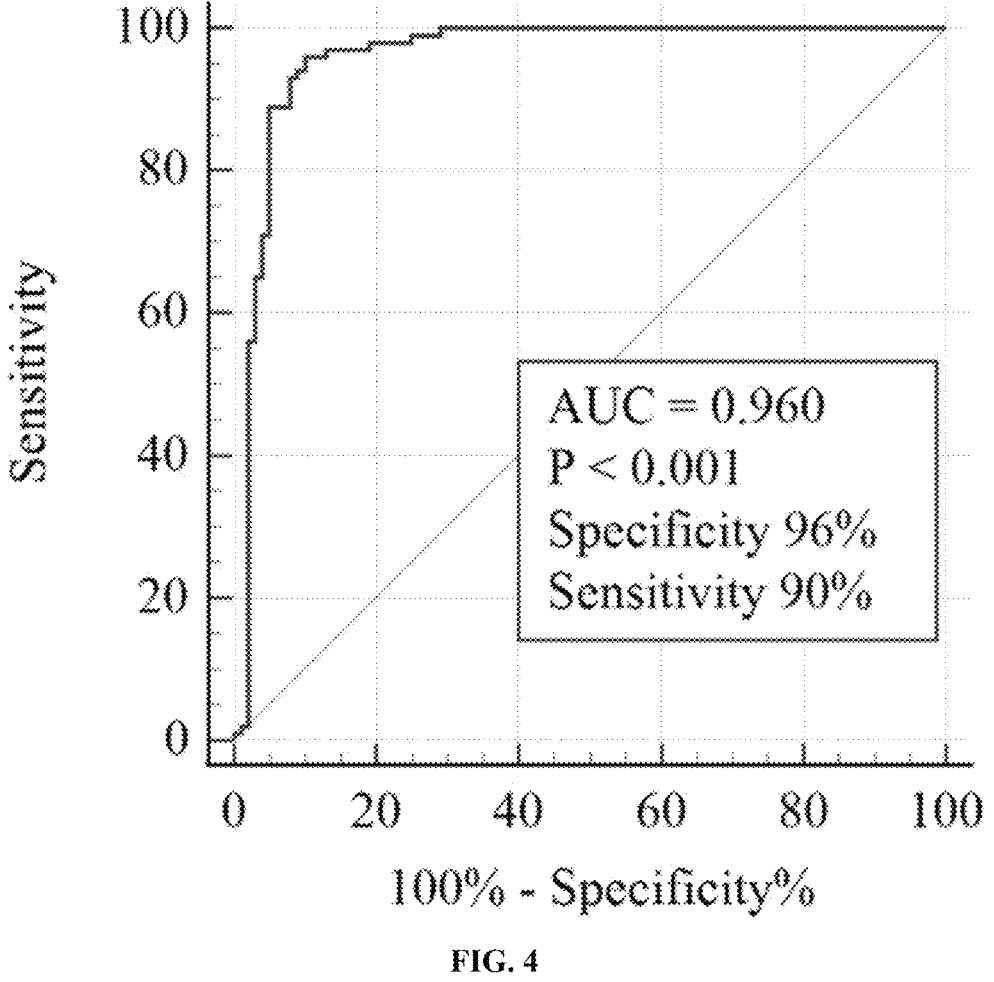
FIG. 4 is a schematic diagram of the ROC curve of the model in the test set.

After the Lasso Logistic regression model was used to construct a gastric cancer incidence risk prediction model in the training set, the AUC of the model in the training set was 0.989, the sensitivity was 91%, and the specificity was 98%, as shown in FIG. 3. The above model was applied to the test set, and the AUC of the model in the test set was 0.96, the sensitivity was 90%, and the specificity was 96%, as shown in FIG. 4. The above results show that the method and the constructed model of the present invention can predict the incidence risk of gastric cancer with relatively high accuracy.

In summary, the present invention obtains a plasma piRNA combination for early diagnosis of gastric cancer based on the plasma piRNA expression profile of the Chinese population, and establishes an early diagnosis model for gastric cancer based on the plasma piRNA combination. The model can predict the incidence risk of gastric cancer with relatively high accuracy, which helps to reduce the cost of detection. At the same time, the present invention uses the Lasso Logistic regression model to greatly reduce the number of variables included in the model, which facilitates the application and popularization of the model.

The above describes an embodiment of the present invention. It can be understood by ordinary technicians in this field. It should be pointed out that various changes, modifications, substitutions and supplements can be made to these embodiments, methodologies and models without departing from the principles and purposes of the present invention, and these changes, modifications, substitutions and supplements should also be regarded as the protection scope of the present invention.

What is claimed is:

1. A method for the early diagnosis of the gastric cancer comprising the following steps:
   (1) collecting plasma from a patient;
   (2) extracting a plasma piwi-interacting RNA (piRNA);
   (3) sequencing small RNA transcriptomes to obtain a plasma piRNA expression profile, wherein the plasma piRNA expression profile comprises hsa-piR-32885, hsa-piR-3440, hsa-piR-786, hsa-piR-12390, hsa-piR-414, hsa-piR-23197, hsa-piR-32911, hsa-piR-32945, hsa-piR-28060, hsa-piR-7096, hsa-piR-32870, and hsa-piR-30778;
   (4) calculating an incidence risk of gastric cancer for the patient according to a Lasso Logistic regression model wherein a mathematical expression of the Lasso Logistic regression model is as follows:

a gastric cancer incidence risk score =

$$\sum (\text{a plasma } piRNA \text{ expression value} \times \text{a regression coefficient}).$$

and identifying a patient having gastric cancer according to the Lasso Logistic regression model; and
   (5) performing an endoscopic biopsy on the patient identified as having gastric cancer according to the Lasso Logistic regression model.

2. The method according to claim 1, wherein the regression coefficient is as follows:

a regression coefficient of the hsa-piR-32885 is-0.001;
a regression coefficient of the hsa-piR-3440 is-0.039;
a regression coefficient of the hsa-piR-786 is-0.007;
a regression coefficient of the hsa-piR-12390 is-0.001;
a regression coefficient of the hsa-piR-414 is-0.002;
a regression coefficient of the hsa-piR-23197 is 0.037;
a regression coefficient of the hsa-piR-32911 is 0.008;
a regression coefficient of the hsa-piR-32945 is 0.004;
a regression coefficient of the hsa-piR-28060 is 0.001;
a regression coefficient of the hsa-piR-7096 is 0.002;
a regression coefficient of the hsa-piR-32870 is 0.002; and
a regression coefficient of the hsa-piR-30778 is 0.026.

3. The method according to claim 1, wherein
the hsa-piR-32885 has the sequence of SEQ ID NO: 1;
the hsa-piR-3440 has the sequence of SEQ ID NO: 2;
the hsa-piR-786 has the sequence of SEQ ID NO: 3;
the hsa-piR-12390 has the sequence of SEQ ID NO: 4;
the hsa-piR-414 has the sequence of SEQ ID NO: 5;
the hsa-piR-23197 has the sequence of SEQ ID NO: 6;
the hsa-piR-32911 has the sequence of SEQ ID NO: 7;
the hsa-piR-32945 has the sequence of SEQ ID NO: 8;
the hsa-piR-28060 has the sequence of SEQ ID NO: 9;
the hsa-piR-7096 has the sequence of SEQ ID NO: 10;
the hsa-piR-32870 has the sequence of SEQ ID NO: 11; and
the hsa-piR-30778 has the sequence of SEQ ID NO: 12.

* * * * *

SEQUENCE LISTING

```
Sequence total quantity: 12
SEQ ID NO: 1               moltype = RNA   length = 28
FEATURE                    Location/Qualifiers
source                     1..28
                           mol_type = other RNA
                           organism = unidentified
SEQUENCE: 1
caccagtgtg agttctacca ttgccaaa                                        28

SEQ ID NO: 2               moltype = RNA   length = 26
FEATURE                    Location/Qualifiers
source                     1..26
                           mol_type = other RNA
                           organism = unidentified
SEQUENCE: 2
tcagacattt ggtgtatgtg cttggc                                          26

SEQ ID NO: 3               moltype = RNA   length = 31
FEATURE                    Location/Qualifiers
source                     1..31
                           mol_type = other RNA
                           organism = unidentified
SEQUENCE: 3
acttgtgatg tcttcaaagg aaccactgat g                                    31

SEQ ID NO: 4               moltype = RNA   length = 28
FEATURE                    Location/Qualifiers
source                     1..28
                           mol_type = other RNA
                           organism = unidentified
SEQUENCE: 4
cagcagttga acatgggtca gtcggtcc                                        28

SEQ ID NO: 5               moltype = RNA   length = 29
FEATURE                    Location/Qualifiers
source                     1..29
                           mol_type = other RNA
                           organism = unidentified
SEQUENCE: 5
acagcagttg aacatgggtc agtcggtcc                                       29

SEQ ID NO: 6               moltype = RNA   length = 31
FEATURE                    Location/Qualifiers
source                     1..31
                           mol_type = other RNA
                           organism = unidentified
SEQUENCE: 6
cctcccaaag tgctgggatt acaggcgtga g                                    31

SEQ ID NO: 7               moltype = RNA   length = 32
FEATURE                    Location/Qualifiers
source                     1..32
                           mol_type = other RNA
                           organism = unidentified
```

```
SEQUENCE: 7
cctggactca agcgatcctc cagcctcagc ct                                    32

SEQ ID NO: 8            moltype = RNA   length = 27
FEATURE                 Location/Qualifiers
source                  1..27
                        mol_type = other RNA
                        organism = unidentified
SEQUENCE: 8
gcgtgcctgt agtcccagct actcggg                                          27

SEQ ID NO: 9            moltype = RNA   length = 26
FEATURE                 Location/Qualifiers
source                  1..26
                        mol_type = other RNA
                        organism = unidentified
SEQUENCE: 9
ggccgtgatc gtatagtggt tagtac                                           26

SEQ ID NO: 10           moltype = RNA   length = 27
FEATURE                 Location/Qualifiers
source                  1..27
                        mol_type = other RNA
                        organism = unidentified
SEQUENCE: 10
tcggcatcaa tatggtgacc tcccggg                                          27

SEQ ID NO: 11           moltype = RNA   length = 26
FEATURE                 Location/Qualifiers
source                  1..26
                        mol_type = other RNA
                        organism = unidentified
SEQUENCE: 11
agggtggttc agtggtagaa ttctcg                                           26

SEQ ID NO: 12           moltype = RNA   length = 27
FEATURE                 Location/Qualifiers
source                  1..27
                        mol_type = other RNA
                        organism = unidentified
SEQUENCE: 12
tactttggga ggctgaggcg ggtggat                                          27
```